(12) United States Patent
Lyapko (10) Patent No.: US 7,267,655 B1
(45) Date of Patent: Sep. 11, 2007

(54) DEVICE FOR REFLEXOTHERAPY

(76) Inventor: Nicolai Grigorievich Lyapko, 8, m-n Sonyachny, app. 21, Krasnogorivka, Marjinsky rayon, Donetskoy obl., 85402 (UA)

( * ) Notice: Subject to any disclaimer, the term of this patent is extended or adjusted under 35 U.S.C. 154(b) by 503 days.

(21) Appl. No.: 10/031,161

(22) PCT Filed: Jul. 13, 2000

(86) PCT No.: PCT/UA00/00022

§ 371 (c)(1),
(2), (4) Date: May 20, 2002

(87) PCT Pub. No.: WO01/05350

PCT Pub. Date: Jan. 25, 2001

(30) Foreign Application Priority Data

Jul. 15, 1999 (UA) .................................. 99074081

(51) Int. Cl.
*A61H 39/00* (2006.01)
(52) U.S. Cl. ...................... 601/134; 606/189
(58) Field of Classification Search ................ 128/907; 606/185, 186, 189; 601/134, 135
See application file for complete search history.

(56) References Cited

U.S. PATENT DOCUMENTS

| | | | | |
|---|---|---|---|---|
| 3,923,064 A * | 12/1975 | Leupold | ...................... | 606/189 |
| 5,158,073 A * | 10/1992 | Bukowski | ...................... | 601/28 |
| 5,250,067 A * | 10/1993 | Gelfer et al. | ................ | 606/189 |
| 5,531,675 A * | 7/1996 | Yoo | ............................. | 604/20 |
| 5,938,684 A * | 8/1999 | Lynch et al. | ................. | 606/204 |
| 5,988,174 A * | 11/1999 | Chasan | ........................ | 128/898 |
| 6,022,368 A * | 2/2000 | Gavronsky et al. | .......... | 606/189 |
| 6,458,146 B1 * | 10/2002 | Kramer | ...................... | 606/204 |

FOREIGN PATENT DOCUMENTS

| CH | 6838225 | * | 5/1994 |
| JP | 7-100181 | * | 4/1995 |
| JP | 10-142360 | * | 5/1998 |
| JP | 11-155926 | * | 6/1999 |

* cited by examiner

*Primary Examiner*—Quang D. Thanh
(74) *Attorney, Agent, or Firm*—Weiner & Burt, P.C.; Irving M. Weiner; Pamela S. Burt (57) ABSTRACT

Reflexotherapy device to stimulate reflex points of the human body provide reliable and integral fastening of needles within an elastic base member to achieve a stable position of needles under any conditions of utilization of the device, and to carry out both static and dynamic impact on extensive areas of reflex zones. The device comprises elastic base member 1 with needles 2 fastened therein each needle being provided with thickened end 3, and sharpened end 4 protruding from base member 1. In one embodiment the needles are fastened in the course of curing of the integral structure and in another embodiment the position of needles 2 is fixed, so that thickened ends are disposed between two layers to be joined together.

12 Claims, 7 Drawing Sheets

DEVICE FOR REFLEXOTHERAPY

FIELD OF INVENTION

The present invention relates to devices used in physiotherapy with the aim of stimulating reflex points on the surface of a human body, and particularly to applicators, and may be used both at medical institutions and under home conditions for practicing reflexotherapy.

BACKGROUND OF THE INVENTION

The closest device to the proposed applicator comprises an applicator having an elastic base member in the form of support and pressure elastic plates that are fastened together, and needles provided with thickened portions (heads) at one ends and sharpened portions at the opposite ends thereof, and passed through the support plate, the thickened portions of said needles being fixed between said plates and protruding above the surface of the support plate with sharpened portions thereof (SU-A-1551381).

Since the support and pressure plates are only fastened together, there exists an interface therebetween; said needles do not form an integral piece, and therefore are insufficiently rigidly fixed within the base member: they can get deepened into the base or protrude therefrom, or tilt around their axes due to the elastic nature of plates and separation of one plate from another, which fact causes insufficient stability of needles position during the use of the applicator. In addition, the need to provide two plates results in a substantial thickness of the base member, thereby resulting in insufficient elasticity thereof.

BRIEF DESCRIPTION OF THE INVENTION

The main object of the present invention consists in improving the applicator by way of clamping the needles in the base member which is made solid in the direction of thickness thereof, thereby providing rigid fixation of needles in the applicator base member and ensuring stability of needles position under any conditions of applicator use, as well as increasing elasticity of the base member.

The object set forth is achieved by that in an applicator comprising an elastic base member and needles, said needles having each an increased thickness at one end and a pointed tip at another end and being fixed in the base member with their portions having the increased thickness and with their portions having the pointed tip projecting from the base member, according to the invention, the elastic base member is made integral in the direction of its thickness and the needles are mounted with their portions having the increased thickness inside of the base member (1) in its plasticized state and squeezed in the process of moulding the integral base member during its setting.

The needles are mounted in the base member with thickened portions (heads) inside of said base member in plasticized state; here, the base material brought to the state of fluidity completely envelops the surface of each needle and tightly clamps said surface during the process of base material curing, i.e. in formation of an integral base member. As a result in the direction of the thickness of the base element there is no a surface which would be parallel to the surfaces of this base member and could divide the base element into two parts, i.e. there is no boundary inside of the base element in the direction of its thickness. Such arrangement provides a rigid fixation of needles in the base member and eliminates the possibility of either their deepening into the base or protruding therefrom or tilting about axes thereof; at the same time stability of needles position under any loads during the use of applicator being provided. Moreover, the use of an integral (in the direction of thickness) base member eliminates the need for two plates, thereby allowing the thickness of the base member to be reduced and its elasticity improved.

The external surface of the base member may be provided with lugs that envelop the needles.

Such arrangement provides further increase in the stability of needles position, particularly in the transverse direction to needles since it increases the length of needle clamping in the base member, while maintaining flexibility of applicator base member and limiting the deepening of needles into user's epidermis.

The needles can be made tapered in the direction from thickened portion toward the sharpened portion thereof, thereby increasing the stability of their position, particularly in the direction perpendicular to the base member surface, since the wedged shape of needles prevents their protrusion from the base member.

In addition, said needles may be provided with thickened portions in the form of heads, thereby further increasing the stability of their position.

The needles may be also made in the form of nails or drawing-pins, thereby simplifying the process of applicator production and making this process cheaper.

The base member of the applicator may be made in the form of a rectangular plate.

Such embodiment of the applicator provides its use in the static mode, i.e. in the mode of permanent action on a predetermined area of the human body.

The base member may be also made in the form of a hollow cylindrical roller which can be either integral in the direction of circumference thereof or rolled up to cylindrical shape from a plate whose edges are butt-fastened together, the needles being mounted in the roller in such way that their sharpened portions protrude from the roller, said roller being fastened to at least one drum mounted for rotation on an axle or fixed to a shaft.

The above embodiment of the applicator in the shape of a roller permits rolling the roller provided with the needles over a corresponding area of the human body, i.e. its use in the dynamic mode, thereby ensuring repeated short-time actions of the needles on reflex points located within this area, which in turn increases the reflexotherapeutic effect, while fastening the needles in a integral roller provides stability of their position under any applicator loads during its use. Making the roller solid in the direction of circumference thereof, using the process of hot or cold placticization (on a mandrel), provides a uniform spiked surface of the applicator and increases its durability, although making the roller production process more complicated. Making the roller by rolling-up the elastic base to a cylinder provides a simpler production process but results in the formation of a seam or a trace thereof between base material edges upon joining them together.

Here, the needles can be mounted on the roller along at least two spaced annular strips.

Such applicator provides the possibility of action of needles on required strip regions of the reflex area while preventing such action on other strip regions (e.g. the possibility of needles action on both sides of the spinal column while eliminating such action on the column itself).

The base member of the applicator can be made in the form of at least two hollow cylindrical rollers which can be either integral direction of circumference thereof or rolled up to cylindrical shape from plates whose edges are butt-fastened together, the needles being mounted in the rollers in such way that their sharpened portions protrude outside from the rollers, said rollers being fastened at intervals to drums, the number of said drums being selected at least equal to the number of rollers, and said drums being mounted for rotation on an axle or fixed to a shaft.

Such applicator also provides the possibility of needles action on external strip regions of a reflex area while eliminating such action on other strip regions (e.g. the possibility of needles action on both sides of the spinal column while eliminating such action on the column itself). In addition, the possibility of independent rotation of the drums relative to the axle provides the possibility of changing the direction of rollers movement without scratching the user's skin.

Butt junction/junctions between plate edges can be made either along the cylinder element or inclined or complex-shaped.

Making butt/butts along the cylinder element provides the simplest process of roller production, while making such butt/butts inclined or complex-shaped increases the strength of butt joints between plate edges.

In addition, the base member of the applicator can be made as a unit-cast roller fixed on a shaft or mounted for rotation on an axle, the needles being mounted in the roller with their sharpened portions protruding outside.

Such embodiment of the applicator base member simplifies its design and manufacture due to elimination of the need in drums but reduces the base member elasticity, thereby resulting in increased probability of scratching user's skin.

Here, the needles may be mounted in the unit-cast roller along at least two spaced annular strips.

The above arrangement provides the possibility of action of needles on required strip regions of the reflex area while preventing such action on other strip regions (e.g. the possibility of needles action on both sides of the spinal column while eliminating such action on the column itself); it however does not provide the possibility of changing the direction of rollers movement without scratching the user's skin since these two strips cannot rotate independently from one another.

Gaps between the above strips can be made in the form of grooves separating said strips.

The base member of the applicator can be made in the form of at least two unit-cast rollers fixed on a shaft or mounted for rotation on an axle in spaced relationship, the needles being mounted in the rollers with their sharpened portions protruding outside.

The axle with drums or rollers mounted thereon can have its end portions protruding beyond applicator end faces or can be provided with a holder with a handle, fixed to said axle, or with at least two brackets fixed on a support member.

The shaft with drums fixed thereon can have its end portions protruding beyond applicator end faces or can be provided with a holder with a handle, fixed to said shaft, or with at least two brackets fixed on a support member, said shaft being mounted in the holder or brackets for rotation.

Protrusion of the ends of the axle or shaft beyond applicator end faces permits the user to roll the roller/rollers while holding same by the protruding ends like a linen beater, thereby simplifying applicator design but limiting the options of its use for certain body areas by the user himself/herself: e.g., he/she cannot treat his/her own back. In addition, it would be difficult to provide a moderate pressure to the body. The holder provided with the handle simplifies the task of rolling since the operation is carried out with one hand; it also extends the opportunities of treating various body areas, and permits provision of a moderate pressure to the body. Mounting the shaft or axle on the brackets that are fixed on a support member allows the applicator to be used for foot soles. Mounting separate rollers on an axle provides their independent rotation and hence ensures the possibility of changing the direction of rollers movement without scratching the user's skin.

The base member of the applicator can be shaped in compliance with a body area to be subjected to reflexotherapy, and provided with coupling members designed to join edges thereof, while the needles can be fixed in the base member in such way that their sharpened portions protrude toward the middle portion of the base member, said needles being mounted either over the whole area or a portion of said base member.

The above embodiment of the base member allows static reflexotherapy of various body areas, e.g. foot soles and palms, to be carried out. With base member edges being separated, the applicator is put on a corresponding body area, following which the edges are engaged, thereby bringing the applicator to contact with the body area and deepening the needles thereinto without any scratching of skin. Placing needles on base member parts allows the required body area to be treated.

Here, the base member can be made as a body of revolution.

Making the base member in the form of a body of revolution, i.e. cylinder, cone, paraboloid etc., with edges provided with coupling members, as well as protrusion of needles in the direction of roller axis permit to envelop the base member around such parts of user's body or separate regions of these parts as shin, thigh, and forearm. In addition, such arrangement of the base member simplifies its manufacture.

BRIEF DESCRIPTION OF DRAWINGS

The invention is further described in more detail and with reference to the accompanying drawings, in which.

PREFERRED EMBODIMENT OF THE INVENTION

Figure 1:
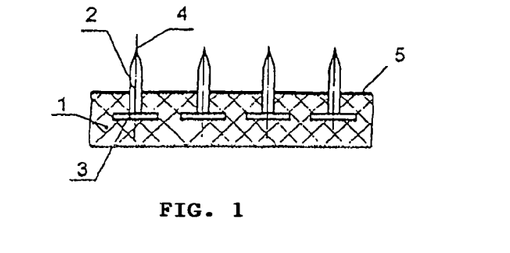
FIG. 1 shows a cross-section of a fragment of the inventive applicator.

Applicator (FIG. 1) comprises base member 1, preferably being elastic (e.g. rubber), and needles 2 with thickened portions 3 (e.g. heads) at one ends and sharpened portions 4 at opposite ends, fixed in said base member 1, needles 2 being fixed in the base member 1 from the side of thickened portions 3 and protruding from surface 5 of base member 1 from the side of sharpened portions 4; needles 2 are clamped in base member 1 by means of hot or cold placticization of said base member 1.

Figure 2:
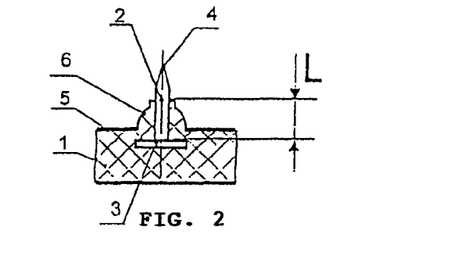
FIG. 2 shows a fragment of the inventive applicator wherein protrusions on the base member envelop needle stems.

In one embodiment of the invention, surface 5 of base member 1 is provided with lugs 6 (FIG. 2) that envelop needles 2. Lugs 6 increase the length, L, of clamping needles 2 in base member 1, thereby improving stability of their position and limiting the deepening of needles into user's epidermis.

Figure 3:
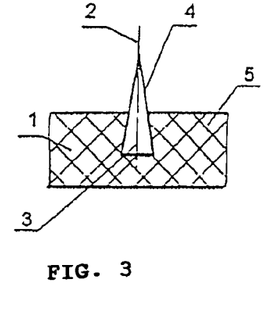
FIG. 3 demonstrates a fragment of the inventive applicator wherein needles are made tapered in the direction toward the sharpened portions.
Figure 4:
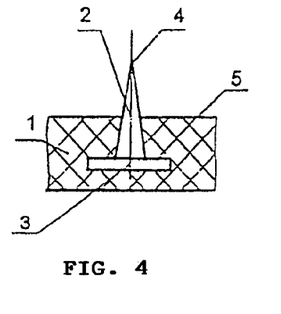
FIG. 4 shows a fragment of the inventive applicator wherein needles are made tapered in the direction toward the sharpened portion and provided with heads on thickened ends.

Needles 2 can be made wedge-shaped, tapered in the direction from thickened portion 3 toward sharpened portion 4 (FIG. 3), i.e. having conical or pyramidal shape, thereby decreasing the possibility of their protrusion beyond surface 5 of base member 1. Here, said thickened portions 3 of needles 2 can be made in the form of heads (FIG. 4).

Figure 5:
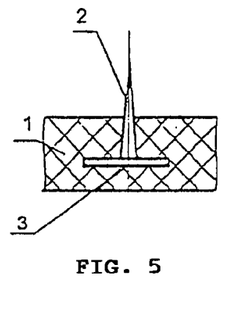
FIG. 5 demonstrates a fragment of the inventive applicator wherein needles are made in the form of drawing-pins.

Needles 2 can be also made in the form of nails (FIG. 1) or drawing-pins (FIG. 5).

The inventive applicator can be made as follows.

Figure 6:
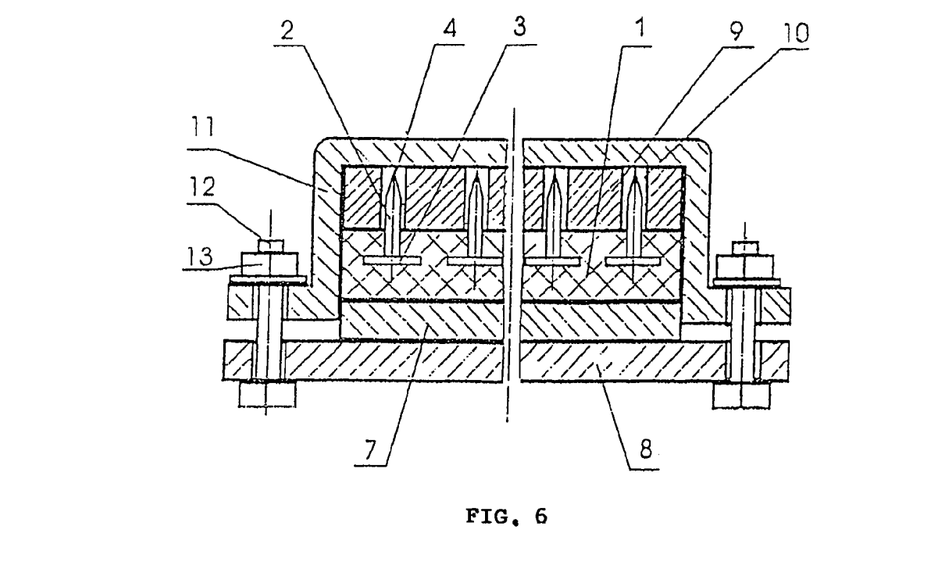
FIG. 6 shows a device for making the inventive applicator in the form of a plate.

Base member 1 of applicator (FIG. 6) is placed on support plate 7, following which they are placed together on support member 8 of the applicator-making device. Mould 9 provided with through openings 10 disposed in compliance with the arrangement of needles 2 in the applicator is placed on the top of base member 1. Needles 2 are inserted into openings 10 with thickened portions 3 (heads) thereof directed toward base member 1 of the applicator. Lid 11 of the applicator-making device is placed on mould 9 and connected by means of bolts 12 and nuts 13 with support member 8 of the applicator-making device. Base member 1 of the applicator is heated up to softening and by means of tightening nuts 13 on bolts 12, a pressure is developed from the side of lid 11 to needles 2; needles 2 are inserted with their thickened portions 3 into base member 1 to a preset depth. Following this, base member 1 is heated up to the hot placticization temperature (particularly, to the temperature of vulcanization of rubber, provided that base member 1 is made of this material). Material of base member 1, being in the state of fluidity, completely envelops the surfaces of needles 2 and, upon cooling of base member 1, tightly clamps needles 2. Upon cooling down support member 8, nuts 13 are unscrewed from bolts 12, lid 11 is removed from support member 8, and base member 1 of applicator with needles 2 clamped therein is released from mould 9 and support member 8 of the applicator-making device. In this way it would be possible to make the inventive applicator.

The applicator of the invention operates as follows.

The applicator is placed in a certain place on a couch; the user is laid onto the applicator with a corresponding reflex area of his/her body. Needles 2 are deepened into the user's epidermis and affect reflex points, thereby providing the necessary effect of reflexotherapy. In addition, the applicator can be fixed to the user's body by means of bandages, belts, or corsets. Needles 2 that are tightly clamped in base member 1 of the applicator keep their position, i.e. do not either deepen into base member 1 or protrude therefrom during any bends of base member 1 and pressures acting on the applicator.

The applicator can be provided with the base member in the form of a hollow cylindrical roller 14 (FIGS. 7, 8) that is solid in the direction of circumference thereof, e.g. a unit-cast roller with needles 2 mounted in roller 14 in such arrangement that their sharpened portions 4 protrude outside, roller 14 being fixed on drums 15 mounted for rotation on axle 16 whose ends 17 protrude beyond end faces 10 of the applicator. Ends 17 can be provided with handles 19.

Figure 8:
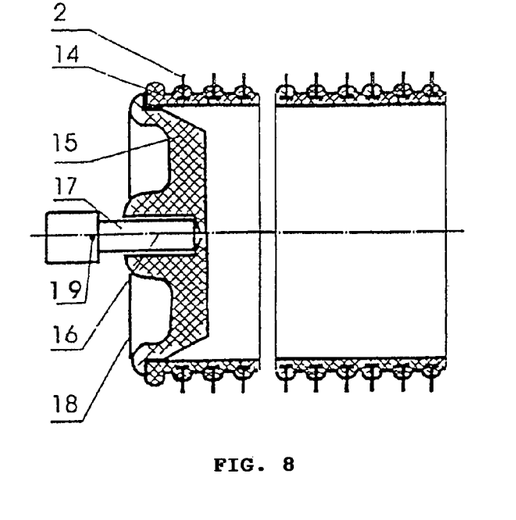
FIG. 8 shows a cross-section of the applicator of FIG. 7.
Figure 9:
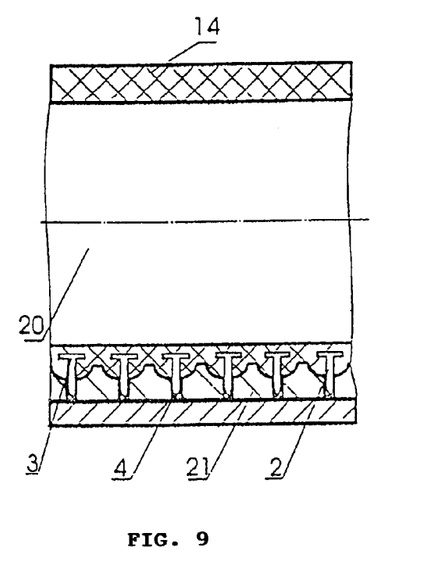
FIGS. 9 and 10 are fragmentary views of the inventive device shaped as a hollow roll solid in circumferential direction, at various stages of making thereof.
Figure 10:
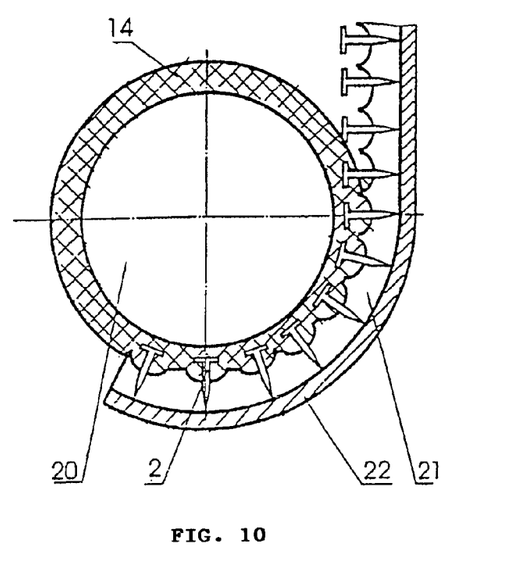

Roller 14 can be made e.g. as follows (see FIGS. 9, 10). The base member in the form of unit-cast roller 14 is mounted on mandrel 20. To mount needles 2 with sharpened portions 4 and head portions 3, the use is made of elastic mould 21 with solid flexible insert 22 abutting against sharpened portions 4 of needles 2, thereby ensuring equal deepening of all needles 2 into roller 14, and with openings (not shown) for needles 2, diameter of said openings slightly exceeding the diameter of needles 2. Mandrel 20 with roller 14 are placed on elastic mould 21 in which needles 2 have been already mounted, upon which said mandrel is heated up to softening of its material. Mould 21 is gradually rotated around roller 14; in so doing, needles 2 are deepened into the body of roller 14 to a depth set by position of insert 22 within the body of mould 21. Material of roller 14 envelops needles 2 and firmly clamps them within the body of roller 14 upon its curing in the process of cooling. After making roller 14 with needles 2 clamped therein, said roller is tightly mounted on drums 15 (FIG. 8).

Figure 11:
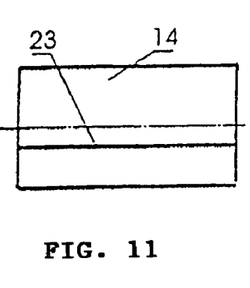
FIGS. 11-13 show optional locations of edge butts of rollers made from plates.
Figure 12:
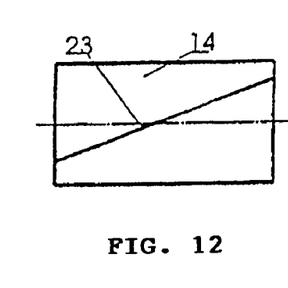
Figure 13:
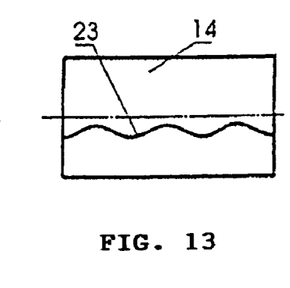

The roller can be also made with the use of a slightly simpler process, i.e. by rolling up a plate made from the base member material to a cylindrical shape, butt-joining the plate edges with the use of placticization or by gluing or by lacing. Here, the butt junction between plate edges is made along cylinder element 23 (FIG. 10) or inclined 24 (FIG. 11) or complex-shaped 25 (FIG. 12).

The applicator operates as follows.

Figure 7:
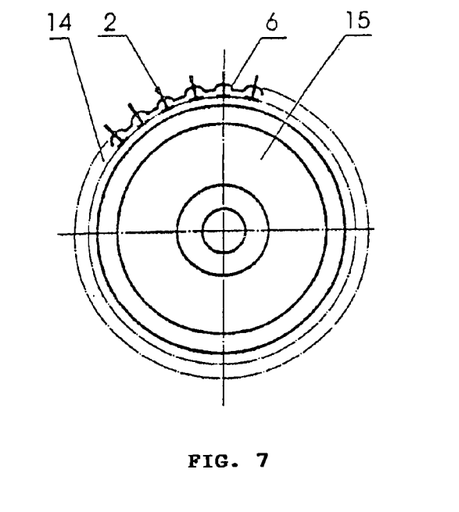
FIG. 7 demonstrates a side view of the inventive applicator in the form of a hollow cylindrical roller.

While holding handles 19 of axle 16 and developing a required pressure to a corresponding area of the body, the user or some other person moves the applicator in reciprocal manner over this area. During this operation, roller 14 with drums 15 rotates around axle 16, deepening needles 2 into and removing them from the user's body, thereby eliminating scratching of user's skin by needles 2. Needles 2 repeatedly and successively affect various reflex points within said area of the user's body, i.e. the applicator operates in the dynamic mode.

Drums 15 (FIG. 14) can be fixed on shaft 26, its ends 27 protruding beyond end faces 28 of roller 14.

Figure 14:
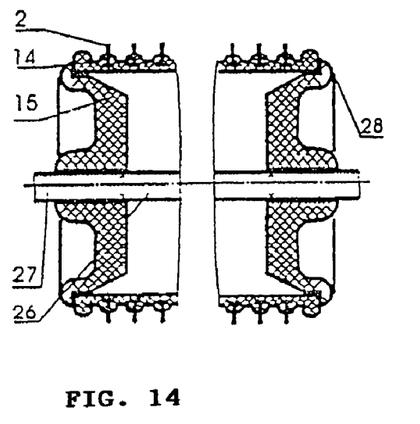
FIGS. 14-15 demonstrate cross-sections of the inventive applicator with drums fixed on the shaft.

Reciprocal motion of the applicator is carried out by reciprocal movements of palms over ends 27 of shaft 26.

Handles 29 (FIG. 15) with stops 30 on handle 29 ends can be mounted for rotation on ends 27 of shaft 26.

Figure 15:
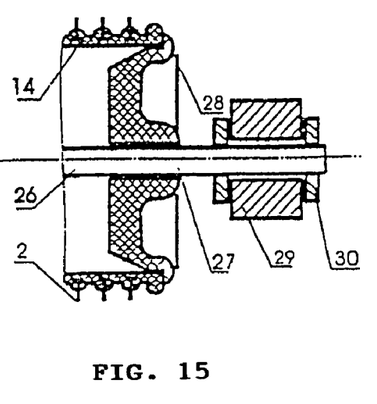

While holding handles 29 of shaft 26 and developing a required pressure to a corresponding area of the body, the user or some other person moves the applicator in reciprocal manner over this area. During this operation, roller 14 with drums 15 and shaft 26 rotates relative to handles 29.

Figure 16:
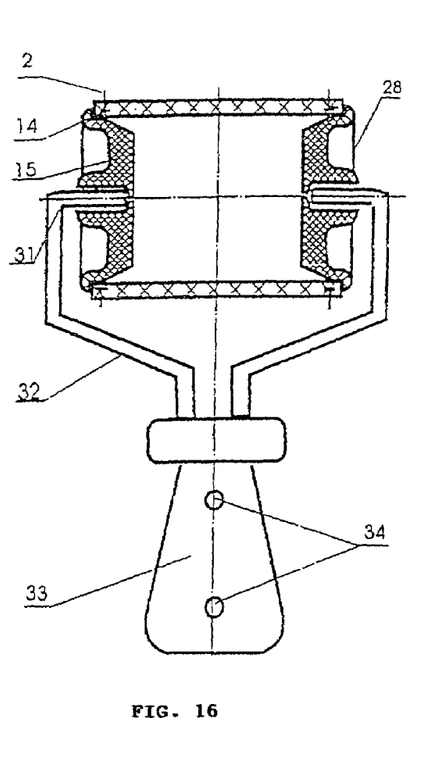
FIG. 16 shows the inventive applicator with drums mounted on an axle provided with a holder.

As shown in FIG. 16, the inventive applicator can be made with the elastic base member in the form of a hollow cylindrical roller 14 with needles 2 fixed in the roller and protruding with sharpened portions thereof beyond the external surface of roller 14. Hollow cylindrical roller 14 is fixed on two drums 15 mounted for rotation on axle 30 having holder 32 with handle 33. Handle 33 consists of two halves fastened together by means of rivets or screws 34 for clamping the ends of holder 32 between the halves of handle 33. In this embodiment, the applicator operates as follows.

While holding handle 33 of holder 32 and developing a required pressure to the user's body, the user or some other person moves the applicator in reciprocal manner over this area, e.g. over the back. In so doing, roller 14 with drums 15 rotates about axle 30, deepening needles 2 into and removing them from the user's body, thereby eliminating scratching of user's skin by needles 2. Needles 2 repeatedly and successively affect various reflex points.

In another embodiment of the invention that can be used e.g. for reflexotherapy of foot soles (FIG. 17), the applicator comprises roller 14 fixed on drums 15 that are mounted for rotation on axle 31. Brackets 35 fixed in support member 36 are made integral with axle 31.

The applicator of this type operates as follows.

Figure 17:
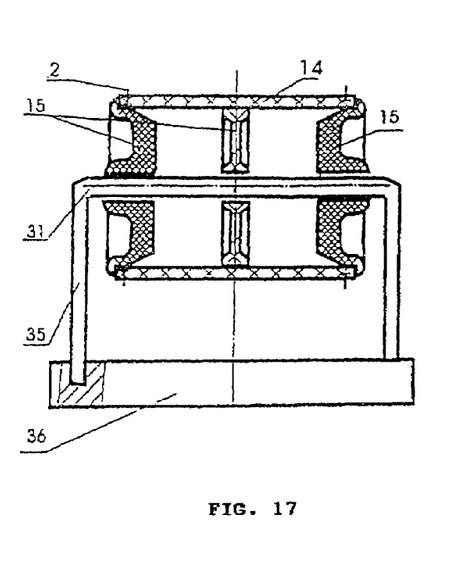
FIG. 17 demonstrates the inventive applicator with drums mounted on an axle provided with brackets fixed on a support.

The user puts his/her one or two soles on needles 2 of roller 14 and by making reciprocal movements, brings roller 14 together with drums 15 to reciprocal-rotational motion about axle 31.

Figure 18:
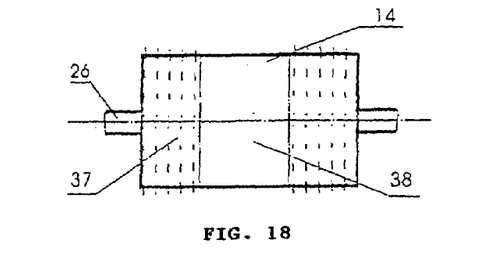
FIG. 18 shows a side view of the roller provided with needles arranged in two strips.

Roller 14 of the applicator (FIG. 18) can be made with needles 2 mounted on roller 14 in the form of at least two annular strips 37 separated by gaps 38.

The user can utilize the applicator for reflexotherapy of individual areas of the body.

According to another preferred embodiment of the invention, the applicator can comprise two rollers 39 (FIG. 19) disposed with gap 40 on drums mounted for rotation on shaft 41 that is provided with holder 42 with handle 43, or can comprise several coaxial rollers 44 (FIG. 20) of the same diameter, having needles 2 and axial gaps 45 between rollers 39. Rollers 39 are fixed on drums 15 that are mounted for rotation about axle 46 provided with holder 47 with handle 48.

Figure 19:
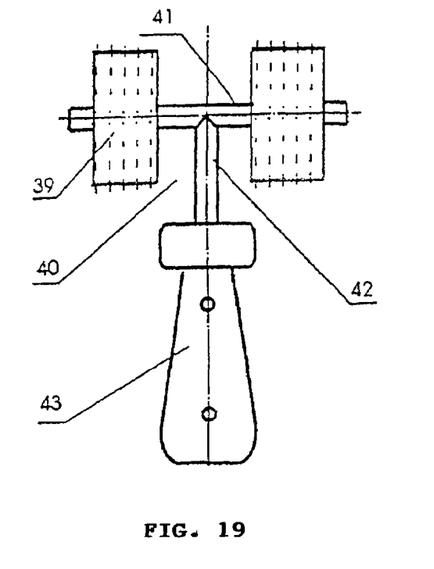
FIG. 19 demonstrates a side view of the inventive applicator with two rollers.
Figure 20:
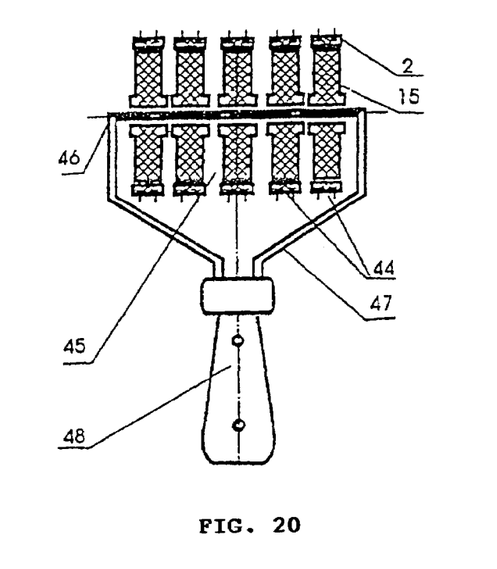
FIG. 20 shows a side view of the inventive applicator with several rollers, drums mounted on the axle, and a holder.

Each of rollers 39 or 44 is made and fixed on drums 15 with the use of the method that has been previously described for one roller 14.

The applicator acts with needles 2 thereof on individual strips of a corresponding reflex area of the human body, leaving the strips between rollers 39 or 44 without action of needles 2. The applicator can be subsequently moved with rollers thereof to different strips, thereby ensuring the required sequence of action of applicator needles 2 on various strips of the reflex area. The applicator provides the possibility of varying the directions of movement of rollers 39 or 44 without scratching the user's skin since rollers 39 or 44 can rotate independently.

Figure 21:
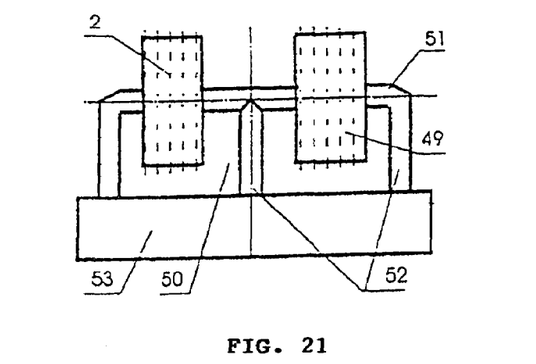
FIG. 21 demonstrates a cross-section of the inventive applicator with several rollers, drums mounted on the axle, and brackets fixed on a support.

In another preferred embodiment of the invention, the applicator is provided with two rollers 49 as shown in FIG. 21. The rollers are mounted with gap 50 on shaft 51 provided with brackets 52 that are fixed on support member 53. Such design is generally used in reflexotherapy of feet; with such arrangement, the user can move feet in opposite directions.

Figure 22:
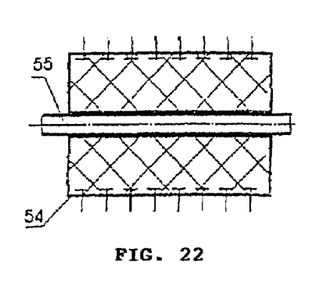
FIG. 22 shows the inventive applicator with a unit-cast roller fixed on a shaft.

The base member of the applicator can be preferably made in the form of unit-cast roller 54 fixed on shaft 55 (FIG. 22). The applicator of this type operates similarly to the applicator shown in FIG. 8 but differs in terms of simplified design and production process.

Figure 23:
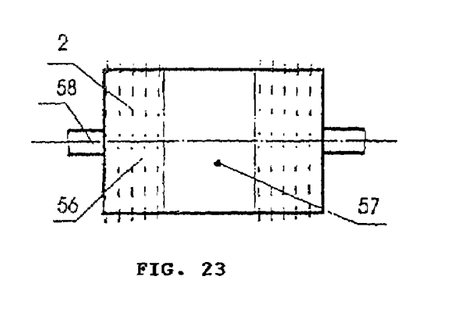
FIG. 23 demonstrates a side view of the inventive applicator with a unit-cast roller provided with needles arranged in two strips.

Needles 2 can be mounted on roller 56 (FIG. 23) along at least two annular strips 57 with gap 58 therebetween. In this embodiment, the applicator operates similarly to the applicator shown in FIG. 18 but also differs in terms of simplified design and production process.

Figure 24:
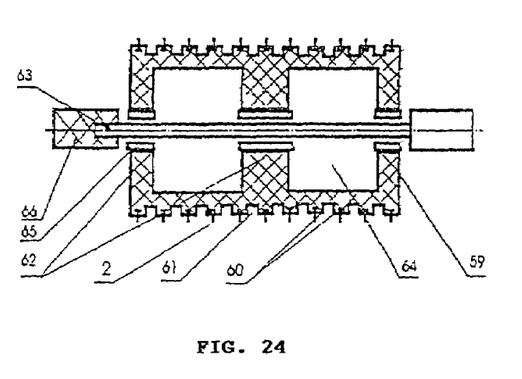
FIG. 24 shows a side view of the applicator with a unit-cast roller mounted on an axle.

Roller 59 of the applicator (FIG. 24) can be preferably provided with strips 60 containing needles 2 and with gaps between strips 60 made in the form of grooves 61. Roller 59 is mounted for rotation by dividers 62 about axle 63. Dividers 62 are formed by indents 64. Sleeves 65 are fixed in the openings of dividers 62. Handles 66 are fixed at the ends of axle 63. The applicator operates similarly to the applicator shown in FIG. 20 but differs in terms of simplified design and production process.

Figure 25:
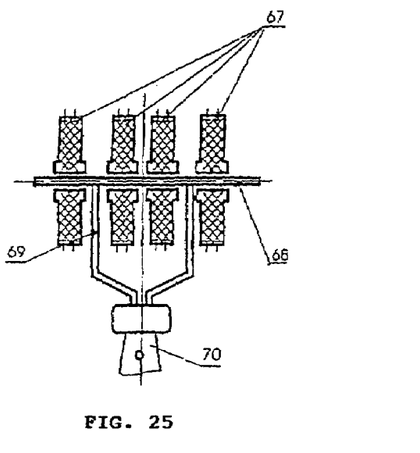
FIG. 25 demonstrates a side view of the inventive applicator with four unit-cast rollers mounted on an axle.

The base member of the applicator can be made in the form of several, e.g. four unit-cast rollers 67 (FIG. 25) mounted for rotation on axle 68 with gaps 69 therebetween. Axle 68 is fixed on holder 69 provided with handle 70. In this embodiment, the applicator operates similarly to the applicator shown in FIG. 20 but also differs in terms of simplified design and production process.

According to still another embodiment of the invention, the base member of the applicator can be shaped in compliance with the body area to be subjected to reflexotherapy, e.g. as a body of revolution, paraboloid 71 (FIG. 26), having axle 72, and provided with coupling members, e.g. zip fastener (FIG. 26) designed to join edges thereof, while needles 2 are mounted in the base member in such way that their sharpened portions 4 protrude toward the middle portion of the base member, i.e. axle thereof, needles 2 being mounted either over the whole area or a portion of said base member.

Figure 27:
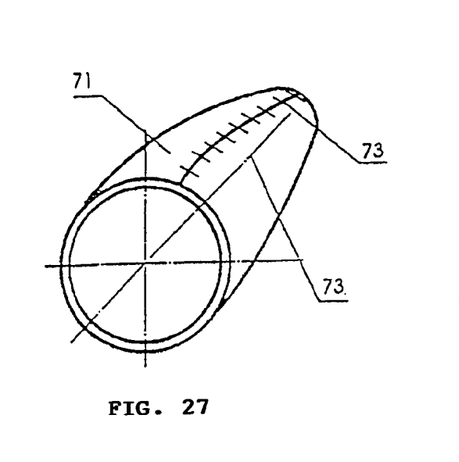
FIG. 27 demonstrates a perspective view of the inventive applicator made in the form of a body of revolution with sharpened portions of the needles directed inside.

During operation of the applicator shown in FIG. 27, zip fastener 73 is unzipped and both halves of paraboloid 71 are placed on a corresponding part of user's body, e.g. on shin. Then zip fastener 73 is zipped; in so doing, needles 2 are deepened into user's shin or a part thereof. After the session of reflexotherapy is over, zip fastener 73 is unzipped, and both halves of paraboloid 71 are removed from the shin.

Figure 28:
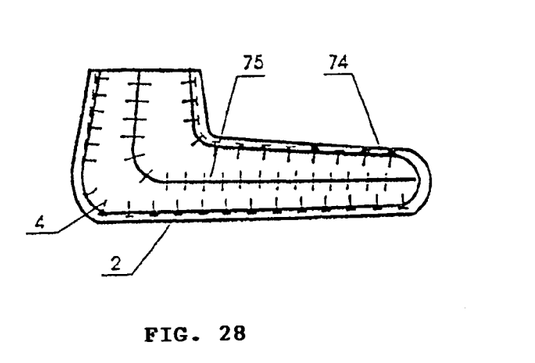
FIG. 28 shows a cross-section of the inventive applicator made in the form of a sock with needles directed inside with sharpened portions thereof.

In addition to the above-mentioned, for the purpose of reflexotherapy of a foot it is possible to use the applicator provided with base member 74 (FIG. 28) matching the foot shape, needles 2 fixed in base member 74 and directed with sharpened portions 4 thereof inside, and zip fastener 75.

Figure 29:
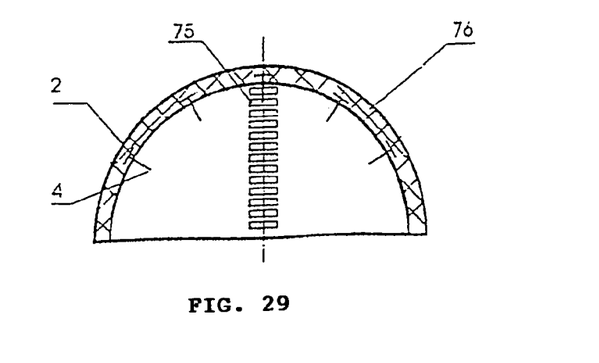
FIG. 29 demonstrates the inventive applicator in the form of a cap with needles directed inside with sharpened portions thereof.

Finally, for the purpose of carrying out reflexotherapy of the upper portion of head, in addition to the above embodiments it is proposed to use the applicator having ball-shaped base member 75, needles 2 with sharpened portions 4 thereof directed to the middle of base member 75, and zip fastener 76.

Figure 26:
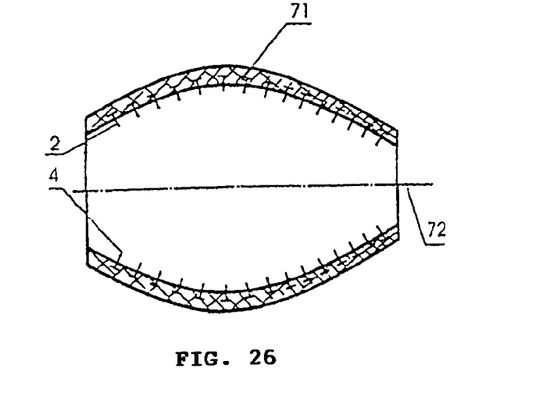
FIG. 26 shows a cross-section of the inventive applicator made in the form of a body of revolution with sharpened portions of the needles directed inside.

Operation of the last two applicators is similar to that shown in FIGS. 26, 27.

The invention claimed is:

1. A device for reflexotherapy, comprising:

an elastic base member being in plasticized condition in the course of heating, and being an integral structure upon curing;

needles provided each with one squeezed thickened end and one sharpened end, said squeezed thickened ends being embedded in said elastic base member when in said plasticized condition so that upon curing of said elastic base member at least said squeezed thickened end of each needle is squeezed in said integral structure of said elastic base member, and said remaining sharpened end of each needle protrudes from said integral structure; and wherein an external surface of said base member is provided with lugs surrounding said needles.

2. The device as claimed in claim 1, wherein:

said needles are made tapered in the direction from said thickened end toward said sharpened end thereof.

3. The device as claimed in claim 2, wherein:

said needles are made with thickened ends in the form of heads.

4. The device as claimed in claim 1, wherein:

said needles are made in the form of nails or drawing pins.

5. A device for reflexotherapy, comprising:

an elastic base member consisting of two layers joined together forming an integral structure in the form of a rectangular plate which is solid in a direction of thickness thereof;

needles provided with one squeezed and tightly clamped thickened end and one sharpened end each;

at least said sharpened end of each needle passing through an upper layer of said two layers of said elastic rectangular plate base member and protruding from a major planar surface of said elastic rectangular plate base member;

said squeezed and tightly clamped thickened end of each needle being disposed between said two layers and joined together with said two layers;

at least said squeezed and tightly clamped thickened end of each needle being squeezed and tightly clamped within said integral structure;

said squeezed and tightly clamped thickened ends being fastened substantially in an area of joint between said two layers; and said elastic rectangular plate base member completely envelops the surface of said squeezed and tightly clamped thickened ends of said needles providing a rigid fixation of said needles in said elastic rectangular plate base member and eliminating tilting of said needles about axes thereof.

6. The device as claimed in claim 5, wherein:

an external surface of said base member is provided with lugs surrounding, contacting and enveloping stems of said needles.

7. The device as claimed in claim 6, wherein:

said needles are made tapered in the direction from said thickened end toward said sharpened end thereof.

8. The device as claimed in claim 7, wherein:

said needles are made with thickened ends in the form of heads.

9. The device as claimed in claim 6, wherein:

said needles are made in the form of nails or drawing pins.

10. The device as claimed in claim 5, wherein:

said needles are made tapered in the direction from said thickened end toward said sharpened end thereof.

11. The device as claimed in claim 10, wherein:

said needles are made with thickened ends in the form of heads.

12. The device as claimed in claim 5, wherein:

said needles are made in the form of nails or drawing pins.

* * * * *